US010640808B2

(12) United States Patent
Gundling et al.

(10) Patent No.: US 10,640,808 B2
(45) Date of Patent: May 5, 2020

(54) SYSTEMS AND METHODS FOR ISOLATING NUCLEIC ACIDS

(71) Applicant: Abbott Molecular Inc., Des Plaines, IL (US)

(72) Inventors: Gerard Gundling, Lake Forest, IL (US); Robert Kowal, Hainesville, IL (US); Edward Granados, Vernon Hills, IL (US); Natalie Solomon, Buffalo Grove, IL (US); Wai-Bing Mak, Cary, IL (US); Magdalena Szostak, Wheeling, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 119 days.

(21) Appl. No.: 14/209,225

(22) Filed: Mar. 13, 2014

(65) Prior Publication Data

US 2014/0272968 A1 Sep. 18, 2014

Related U.S. Application Data

(60) Provisional application No. 61/780,236, filed on Mar. 13, 2013.

(51) Int. Cl.
*C12Q 1/6806* (2018.01)
*C12N 15/10* (2006.01)
*C12N 1/06* (2006.01)

(52) U.S. Cl.
CPC ............. *C12Q 1/6806* (2013.01); *C12N 1/06* (2013.01); *C12N 15/1003* (2013.01)

(58) Field of Classification Search
CPC .... C12Q 1/68; C12Q 1/6806; C12N 15/1003; G01N 1/34; C07H 21/00; C12P 19/34
See application file for complete search history.

(56) References Cited

U.S. PATENT DOCUMENTS

| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,075,430 A * | 12/1991 | Little ................. C12N 15/1006 423/335 |
| 5,130,238 A | 7/1992 | Malek et al. |
| 5,234,809 A * | 8/1993 | Boom .................... C07H 21/00 422/504 |
| 5,270,184 A | 12/1993 | Walker et al. |
| 5,283,174 A | 2/1994 | Arnold, Jr. et al. |
| 5,399,491 A | 3/1995 | Kacian et al. |
| 5,455,166 A | 10/1995 | Walker |
| 5,480,784 A | 1/1996 | Kacian et al. |
| 5,637,687 A * | 6/1997 | Wiggins ............. C12N 15/1003 435/270 |
| 5,695,934 A | 12/1997 | Brenner |
| 5,705,628 A * | 1/1998 | Hawkins ............ C12N 15/1013 252/62.51 R |
| 5,710,029 A | 1/1998 | Ryder et al. |
| 5,714,330 A | 2/1998 | Brenner et al. |
| 5,750,341 A | 5/1998 | Macevicz |
| 5,786,146 A | 7/1998 | Herman et al. |
| 5,807,527 A | 9/1998 | Burgoyne |
| 5,808,041 A | 9/1998 | Padhye et al. |
| 5,814,447 A | 9/1998 | Ishiguro et al. |
| 5,824,518 A | 10/1998 | Kacian et al. |
| 5,925,517 A | 7/1999 | Tyagi et al. |
| 5,928,862 A | 7/1999 | Morrison |
| 6,150,097 A | 11/2000 | Tyagi et al. |
| 6,168,922 B1 | 1/2001 | Harvey et al. |
| 6,180,778 B1 * | 1/2001 | Bastian .............. C12N 15/1006 536/25.3 |
| 6,303,305 B1 | 10/2001 | Wittwer et al. |
| 6,306,597 B1 | 10/2001 | Macevicz |
| 6,432,360 B1 | 8/2002 | Church |
| RE37,891 E | 10/2002 | Collins et al. |
| 6,485,944 B1 | 11/2002 | Church et al. |
| 6,511,803 B1 | 1/2003 | Church et al. |
| 6,534,274 B2 | 3/2003 | Becker et al. |
| 6,541,205 B1 | 4/2003 | Yokoyama et al. |
| 6,673,631 B1 * | 1/2004 | Tereba ............... C12N 15/1013 423/335 |
| 6,787,308 B2 | 9/2004 | Balasubramanian et al. |
| 6,833,246 B2 | 12/2004 | Balasubramanian |
| 6,992,782 B1 * | 1/2006 | Yardumian ........... G06F 3/1206 358/1.13 |
| 7,108,974 B2 | 9/2006 | Ecker et al. |

(Continued)

FOREIGN PATENT DOCUMENTS

| EP | 0684315 A1 | 11/1995 |
| EP | 2210936 | 7/2010 |

(Continued)

OTHER PUBLICATIONS

Eads et al., Methylight: a high-throughput assay to measure DNA methylation. Nucleic Acids Research 28(8) : e32 (2000).*
Heid et al.,Real Time Quantitative PCR. Genome Research 6 : 986 (1996).*
Kopreski et al.,Detection of mutant K-ras DNA in plasma or serum of patients with colorectal cancer. British J. of Cancer 76 (10) : 1293 (1997).*
Maire et al., Differential diagnosis between chronic pancreatitis and pancreatic cancer: value of the detection of KRAS2 mutations in circulating DNA. British J. of Cancer 87 :551 (2002).*
Su et al., Human Urine Contains Small, 150 to 250 Nucleotide-Sized, Soluble DNA Derived from the Circulation and May Be Useful in the Detection of Colorectal Cancer. J. of Molecular Diagnostics 6 (2) : 101 (2004).*

(Continued)

*Primary Examiner* — Ethan C Whisenant
(74) *Attorney, Agent, or Firm* — Casimir Jones S.C.; Kirk Hogan

(57) ABSTRACT

The present disclosure relates to systems and methods for nucleic acid isolation. In particular, the present disclosure provides systems and methods for isolating low molecular weight circulating nucleic acids from bodily fluids (e.g., plasma).

16 Claims, No Drawings

(56) References Cited

U.S. PATENT DOCUMENTS

| | | | |
|---|---|---|---|
| 7,262,006 B1* | 8/2007 | Belly | C12Q 1/6806 435/270 |
| 7,524,629 B2 | 4/2009 | Olek et al. | |
| 8,008,475 B1* | 8/2011 | Bastian | C12Q 1/6806 210/650 |
| 8,017,322 B2 | 9/2011 | Ecker et al. | |
| 8,017,743 B2 | 9/2011 | Ecker et al. | |
| 8,734,364 B1* | 5/2014 | Mantzaris | A61B 5/4362 600/572 |
| 9,012,146 B2 | 4/2015 | Heckel et al. | |
| 2002/0064786 A1* | 5/2002 | Markowitz | C07K 14/71 435/6.11 |
| 2003/0083339 A1* | 5/2003 | Tamura | A61K 31/401 514/263.4 |
| 2003/0087397 A1* | 5/2003 | Klein | C12Q 1/6818 435/91.1 |
| 2004/0111760 A1* | 6/2004 | Chia | C12N 9/1029 800/278 |
| 2004/0157223 A1* | 8/2004 | Lou | C07H 21/04 435/6.11 |
| 2005/0042638 A1 | 2/2005 | Arnold et al. | |
| 2005/0059024 A1* | 3/2005 | Conrad | C12N 15/1003 435/6.12 |
| 2005/0106577 A1* | 5/2005 | Akhavan-Tafti | C07H 21/04 435/6.16 |
| 2005/0130173 A1 | 6/2005 | Leamon et al. | |
| 2005/0202490 A1 | 9/2005 | Makarov et al. | |
| 2005/0208037 A1* | 9/2005 | Dashnamoorthy | A61K 31/704 424/94.4 |
| 2005/0208510 A1* | 9/2005 | Latham | C12N 15/1006 435/6.12 |
| 2005/0239068 A1* | 10/2005 | Bosnes | G01N 33/54306 435/6.18 |
| 2006/0046265 A1 | 3/2006 | Becker et al. | |
| 2006/0240409 A1* | 10/2006 | Prince | C07H 21/02 435/5 |
| 2007/0243542 A1* | 10/2007 | Belly | C12N 15/1003 435/6.12 |
| 2008/0132694 A1* | 6/2008 | Himmelreich | C12N 15/1013 536/25.41 |
| 2009/0048439 A1* | 2/2009 | Weisburg | C12N 15/1006 536/25.41 |
| 2009/0215125 A1* | 8/2009 | Reed | B01L 3/5027 435/91.2 |
| 2009/0277791 A1* | 11/2009 | Vu | G01N 33/559 204/461 |
| 2010/0140110 A1* | 6/2010 | Kim | B01L 3/502761 205/775 |
| 2011/0172409 A1* | 7/2011 | Han | C12N 15/1006 536/25.4 |
| 2011/0245483 A1* | 10/2011 | Euting | C12N 15/1013 536/25.41 |
| 2011/0300608 A1* | 12/2011 | Ryan | C12N 15/1003 435/270 |
| 2012/0164648 A1* | 6/2012 | Han | C12N 15/1003 435/6.12 |
| 2012/0237939 A1* | 9/2012 | Reed | B01L 3/5027 435/6.12 |
| 2012/0301926 A1* | 11/2012 | Chen | C12Q 1/6806 435/91.5 |
| 2013/0303746 A1* | 11/2013 | Ruegg | C12N 15/1003 536/25.42 |

FOREIGN PATENT DOCUMENTS

| | | |
|---|---|---|
| WO | WO-9500669 A1 | 1/1995 |
| WO | WO-9515373 A2 | 6/1995 |
| WO | WO-9745560 A1 | 12/1997 |
| WO | WO-9746705 A1 | 12/1997 |
| WO | WO-9928498 A2 | 6/1999 |
| WO | WO-0018957 A1 | 4/2000 |
| WO | WO-2006084132 A2 | 8/2006 |
| WO | 2008116182 | 9/2008 |
| WO | 2009102632 | 8/2009 |

OTHER PUBLICATIONS

Eads et al., Methylight: a high-throughput assay to measure DNA methylation. Nucleic Acids Research 28(8) : e32 (2000).—Provided in U.S. Appl. No. 14/209,225.*

Heid et al., Real Time Quantitative PCR. Genome Research 6 : 986 (1996).—Provided in U.S. Appl. No. 14/209,225.*

Herman et al., Methylation-specific PCR: a novel PCR assay for methylation status of CpG islands. PNAS 93 : 9821 (1996).—Provided in U.S. Appl. No. 14/212,880.*

Kopreski et al., Detection of mutant K-ras DNA in plasma or serum of patients with colorectal cancer. British J. of Cancer 76 (10) : 1293 (1997).—Provided in U.S. Appl. No. 14/209,225.*

Maire et al., Differential diagnosis between chronic pancreatitis and pancreatic cancer: value of the detection of KRAS2 mutations in circulating DNA. British J. of Cancer 87: 551 (2002).—Provided in U.S. Appl. No. 14/209,225.*

Saiyed et al., Application of magnetic particles (Fe3O4) for isolation of genomic DNA from mammalian cells. Analytical Biochemistry 356 : 306 (2006). Provided in U.S. Appl. No. 14/212,880.*

Saiyed et al., Extraction of DNA from agarose gel using magnetic nanoparticles (magnetite or Fe3O4). Analytical Biochemistry 363 : 288 (2007). Provided in U.S. Appl. No. 14/212,880.*

Su et al., Human Urine Contains Small, 150 to 250 Nucleotide-Sized, Soluble DNA Derived from the Circulation and May Be Useful in the Detection of Colorectal Cancer. J. of Molecular Diagnostics 6 (2) : 101 (2004).—Provided in U.S. Appl. No. 14/209,225.*

Tan et al., Review Article : DNA, RNA, and Protein Extraction: The Past and the Present Journal of Biomedicine and Biotechnology 2009: 10 pages. Provided in U.S. Appl. No. 14/212,880.*

Taylor et al. Application of magnetite and silica-magnetite composites to the isolation of genomic DNA. Journal of Chromatogrphy A 890: 159 (2000). Provided in U.S. Appl. No. 14/212,880.*

Yang et al. Magnetite-Containing Spherical Silica Nanoparticles for Biocatalysis and Bioseparations. Analytical Chemistry 76 : 1316 (2004). Provided in U.S. Appl. No. 14/212,880.*

The Stratagene Catalog p. 39 (1988). Cited and copy provided in copending U.S. Appl. No. 14/209,166.*

Berensmeier, S., Magnetic particles for the separation and purification of nucleic acids. Appl. Microbiol. Biotechnol. 73 : 495 (2006).*

Chiu et al., Effects of Blood-Processing Protocols on Fetal and Total DNA Quantification in Maternal Plasma. Clinical Chemistry 47(9) :1607 (2001).*

Giacona et al., Cell-Free DNA in Human Blood Plasma: Length Measurements in Patients with Pancreatic Cancer and Healthy Controls. Pancreas 17(1) : 89 (1998).*

Huang et al., Isolation of Cell-Free DNA from Maternal Plasma Using Manual and Automated Systems . Methods in Molecular Biology 444 :203 (2008). Edited by Hahn et al. Humana Press.*

Rofe, P., The cells of Normal urine. J. of Clinical Pathology 8 : 25 (1955).*

Heid et al., Real Time Quantitative PCR. Gnome Research 6 :986-994 (1996).*

Jorgez et al., Quantity versus quality: Optimal methods for cell-free DNA isolation from plasma of pregnant women. Genetics in Medicine 8 (10) : 615-619 (2006).*

McLaughlin et al., Are There Naturally Occurring Pleomorphic Bacteria in the Blood of Healthy Humans? J. of Clinical Microbiology 40 (12) : 4771-4775 (2002).*

Berensmeier; Magnetic particles for the separation and purification of nucleic acids. Applied Microbiology and Biotechnology 73 :495 (Year: 2006).*

Cottrell et al., A real-time PCR assay for DNA-methylation using methylation-specific blockers. Nucleic Acids Research 32(1) : e 10 (Year: 2004).*

(56) References Cited

OTHER PUBLICATIONS

Mouliere et al., High Fragmentation Characterizes Tumour-Derived Circulating DNA.. Plos One 6(9) : e23418 (Year: 2011).*
Adessi C., et al., "Solid Phase DNA Amplification: Characterisation of Primer Attachment and Amplification Mechanisms," Nucleic Acids Research, 2000, vol. 28 (20), pp. E87.
Bennett S.T., et al., "Toward the 1,000 Dollars Human Genome," Pharmacogenomics, 2005, vol. 6 (4), pp. 373-382.
Branton D., et al., "The Potential and Challenges of Nanopore Sequencing," Nature Biotechnology, 2008, vol. 26 (10), pp. 1146-1153.
Brenner S., et al., "Gene Expression Analysis by Massively Parallel Signature Sequencing (MPSS) on Microbead Arrays," Nature Biotechnology, 2000, vol. 18 (6), pp. 630-634.
Chan K.C.A., et al., "Circulating Tumour-Derived Nucleic Acids in Cancer Patients: Potential Applications as Tumour Markers," British Journal of Cancer, 2007, vol. 96, pp. 681-685.
Drmanac S., et al., "Accurate Sequencing by Hybridization for DNA Diagnostics and Individual Genomics," Nature Biotechnology, 1998, vol. 16 (1), pp. 54-58.
Eads C.A., et al., "CpG Island Hypermethylation in Human Colorectal Tumors Is Not Associated with DNA Methyltransferase Overexpression," Cancer Research, 1999, vol. 59, pp. 2302-2306.
Eid J., et al., "Real-time DNA Sequencing from Single Polymerase Molecules," Science, 2009, vol. 323 (5910), pp. 133-138.
Feil R., et al., "Methylation Analysis on Individual Chromosomes: Improved Protocol for Bisulphite Genomic Sequencing," Nucleic Acids Research, 1994, vol. 22 (4), pp. 695-696.
Fleischhacker M., et al., "Circulating Nucleic Acids (CNAS) and Cancer—A Survey," Biochimica et Biophysica Acta, 2007, vol. 1775 (1), pp. 181-232.
Gonzalgo M.L., et al., "Rapid Quantitation of Methylation Differences at Specific Sites Using Methylation-Sensitive Single Nucleotide Primer Extension (MS-SNuPE)," Nucleic Acids Research, 1997, vol. 25 (12), pp. 2529-2531.
Grigg G., et al., "Sequencing 5-methylcytosine Residues in Genomic DNA," BioEssays, 1994, vol. 16 (6), pp. 431-436.
Guatelli J.C., et al., "Isothermal, in Vitro Amplification of Nucleic Acids by a Multienzyme Reaction Modeled after Retroviral Replication," Proceedings of the National Academy of Sciences, 1990, vol. 87 (5), pp. 1874-1878.
Harris T.D., et al., "Single-molecule Dna Sequencing of a Viral Genome," Science, 2008, vol. 320 (5872), pp. 106-109.
Hennig G., et al., "Mechanisms Identified in the Transcriptional Control of Epithelial Gene Expression," The Journal of Biological Chemistry, 1996, vol. 271 (1), pp. 595-602.
Herman J.G., et al., "Methylation-Specific PCR: A Novel PCR Assay for Methylation Status of Cpg Islands," Proceedings of the National Academy of Sciences, 1996, vol. 93 (18), pp. 9821-9826.
Hu X.C., et al., "E-Cadherin Promoter Methylation Can Regulate its Expression in Invasive Ductal Breast Cancer Tissue in Chinese Woman," Life Science, 2002, vol. 71 (12), pp. 1397-1404.
International Search Report and Written Opinion for Application No. PCT/US14/26106, dated May 21, 2014, 17 pages.
Kato K., "Impact of the Next Generation Dna Sequencers," International Journal of Clinical and Experimental Medicine, 2009, vol. 2 (2), pp. 193-202.
Korlach J., et al., "Selective Aluminum Passivation for Targeted Immobilization of Single DNA Polymerase Molecules in Zero-Mode Waveguide Nanostructures," Proceedings of the National Academy of Sciences, 2008, vol. 105 (4), pp. 1176-1181.
Kumagai Y., et al., "Histone Deacetylase Inhibitor, Suberoylanilide Hydroxamic Acid (Vorinostat, SAHA) Profoundly Inhibits the Growth of Human Pancreatic Cancer Cells," International Journal of Cancer, 2007, vol. 121 (3), pp. 656-665.
Kwoh D.Y., et al., "Transcription-Based Amplification System and Detection of Amplified Human Immunodeficiency Viru: Type 1 with a Bead-Based Sandwixh Hybridization Format," Proceeding of the National Academy of Sciences of the USA, 1989, vol. 86 (4), pp. 1173-1177.
Levene M.J., et al., "Zero-mode Waveguides for Single-molecule Analysis at High Concentrations," Science, 2003, vol. 299 (5607), pp. 682-686.
Lind G.E., et al., "A CpG Island Hypermethylation Profile of Primary Colorectal Carcinomas and Colon Cancer Cell Lines," Molecular Cancer, 2004, vol. 3:28, 11 pages.
Lizardi P.M., et al., "Exponential Amplification of Recombinant-RNA Hybridization Probes," Bio/Technology, 1988, vol. 6, pp. 1197-1202.
Lombaerts M., et al., "E-Cadherin Transcriptional Downregulation by Promoter Methylation but Not Mutation is Related to Epithelial-to-Mesenchymal Transition in Breast Cancer Cell," British Journal of Cancer, 2006, vol. 94 (5), pp. 661-671.
Maclean D., et al., "Application of 'next-generation' Sequencing Technologies to Microbial Genetics," Nature Reviews Microbiology, 2009, vol. 7 (4), pp. 287-296.
Marchevsky A.M., et al., "Classification of Individual Lung Cancer Cell Lines Based on DNA Methylation Markers: Use of Linear Discriminant Analysis and Artificial Neural Networks," Journal of Molecular Diagnostics, 2004, vol. 6 (1), pp. 28-36.
Margulies M., et al., "Genome Sequencing in Microfabricated High-Density Picolitre Reactors," Nature, 2005, vol. 437 (7057), pp. 376-380.
Martin V., et al., "Genomic Sequencing Indicates a Correlation Between DNA Hypomethylation in the 5' Region of the Ps2 Gene and its Expression in Human Breast Cancer Cell Lines," Gene, 1995, vol. 157 (1-2), pp. 261-264.
Maxam A.M., et al., "A New Method for Sequencing Dna," Proceedings of the National Academy of Sciences of the United States of America, 1977, vol. 74 (2), pp. 560-564.
Mitra R.D., et al., "Fluorescent in Situ Sequencing on Polymerase Colonies," Analytical Biochemistry, 2003, vol. 320 (1), pp. 55-65.
Morozova O., et al., "Applications of Next-generation Sequencing Technologies in Functional Genomics," Genomics, 2008, vol. 92 (5), pp. 255-264.
Mullis K.B., et al., "Specific Synthesis of DNA In Vitro via a Polymerase-catalyzed Chain Reaction," Methods in Enzymology, 1987, vol. 155, pp. 335-350.
Murakawa G.J., et al., "Direct Detection of HIV-1 RNA from AIDS and ARC Patient Samples," DNA: A Journal of Molecular Biology, 1988, vol. 7 (4), pp. 287-295.
Nakata S., et al., "The Methylation Status and Protein Expression of CDH1, P16 (INK4A), and Fragile Histidine Triad in Nonsmall Cell Lung Carcinoma: Epigenetic Silencing, Clinical Features, and Prognostic Significance," Cancer, 2006, vol. 106 (10), pp. 2190-2199.
Nelson N. C., et al., "Detection of Acridinium Esters by Chemiluminescence," in: Nonisotopic Probing, Blotting and Sequencing, 1995, Chapter 17, Academic Press, Inc., pp. 391-428.
Olek A., et al., "The Pre-Implantation Ontogeny of the H19 Methylation Imprint," Nature Genetics, 1997, vol. 17, pp. 275-276.
Persing, "In Vitro Nucleic Acid Amplification Techniques," Diagnostic Molecular Microbiology, 1993, pp. 51-77.
Rein T., et al., "Identifying 5-Methylcytosine and Related Modifications in DNA Genomes," Nucleic Acids Research, 1998, vol. 26 (10), pp. 2255-2264.
Reinhold W.C., et al., "Detailed DNA Methylation Profiles of the E-Cadherin Promoter in the NCI-60 Cancer Cells," Molecular Cancer Therapeutics, 2007, vol. 6 (2), pp. 391-403.
Ronaghi M., et al., "Real-time Dna Sequencing Using Detection of Pyrophosphate Release," Analytical Biochemistry, 1996, vol. 242 (1), pp. 84-89.
Ruparel H., et al., "Design and Synthesis of A 3'-o-allyl Photocleavable Fluorescent Nucleotide as a Reversible Terminator for Dna Sequencing by Synthesis," Proceedings of the National Academy of Sciences of the United States of America, 2005, vol. 102 (17), pp. 5932-5937.
Sambrook J., et al., eds., Molecular Cloning: A Laboratory Manual, 3rd Edition, Cold Spring Harbor Laboratory, 2001, Table of Contents.
Sanger F., et al., "Dna Sequencing with Chain-Terminating Inhibitors," Proceedings of the National Academy of Sciences, 1977, vol. 74 (12), pp. 5463-5467.

(56) References Cited

OTHER PUBLICATIONS

Sayres L.C., et al., "Cell-Free Fetal Nucleic Acid Testing: A Review of the Technology and its Applications," Obstetrical & Gynecological Survey, 2011, vol. 66 (7), pp. 431-442.

Schwarzenbach A., et al., "Cell-Free Nucleic Acids as Biomarkers in Cancer Patients," Nature Reviews Cancer, 2011, vol. 11, pp. 426-437.

Shendure J., et al., "Accurate Multiplex Polony Sequencing of an Evolved Bacterial Genome," Science, 2005, vol. 309 (5741), pp. 1728-1732.

Voelkerding K.V., et al., "Next-Generation Sequencing: from Basic Research to Diagnostics," Clinical Chemistry, 2009, vol. 55 (4), pp. 641-658.

Walker G.T., et al., "Isothermal in Vitro Amplification of DNA by a Restriction Enzyme/DNA Polymerase System," Proceedings of the National Academy of Sciences, 1992, vol. 89 (1) pp. 392-396.

Weiss R., "Hot Prospect for New Gene Amplifier," Science, 1991, vol. 254 (5036), pp. 1292-1293.

Xiong Z., et al., "COBRA: A Sensitive and Quantitative DNA Methylation Assay," Nucleic Acids Research, 1997, vol. 25 (12), pp. 2532-2534.

Yoshiura K., et al., "Silencing of the E-Cadherin Invasion-Suppressor Gene by Cpg Methylation in Human Carcinomas," Proceedings of the National Academy of Sciences, 1995, vol. 92 (16), pp. 7416-7419.

Zeschnigk M., et al., "Imprinted Segments in the Human Genome: Different DNA Methylation Patterns in the Prader-Willi/Angelman Syndrome Region as Determined by the Genomic Sequencing Method," Human Molecular Genetics, 1997, vol. 6 (3), pp. 387-395.

Qiagen GMBH: "QIAamp Circulating Nucleic Acid Handbook", Internet Citation, 2011, pp. 1-56, XP002753499, [retrieved on Jan. 1, 2011], Retrieved from the Internet.

Supplementary European search report for Application No. EP14772979, dated Sep. 26, 2016, 6 pages.

EPO Communication issued for corresponding European Application No. EP14772979, dated Jun. 29, 2018, 6 pages.

Office Action issued for corresponding Application No. EP14772979.2, dated Nov. 11, 2019, 7 pages.

\* cited by examiner

SYSTEMS AND METHODS FOR ISOLATING NUCLEIC ACIDS

This application claims priority to Provisional Patent Application Ser. No. 61/780,236, filed Mar. 13, 2013, which is herein incorporated by reference in its entirety.

FIELD OF INVENTION

The present disclosure relates to systems and methods for nucleic acid isolation. In particular, the present disclosure provides systems and methods for isolating low molecular weight circulating nucleic acids from bodily fluids (e.g., plasma).

BACKGROUND

Nucleic acids found in cells can be deoxyribonucleic acid or ribonucleic acid and can be genomic DNA, extrachromosomal DNA (e.g. plasmids and episomes), mitochondrial DNA, messenger RNA, miRNA, and transfer RNA. Nucleic acids can also be foreign to the host and contaminate a cell as an infectious agent, e.g. bacteria, viruses, fungi or single celled organisms and infecting multicellular organisms (parasites). Recently, detection and analysis of the presence of nucleic acids has become important for the identification of single nucleotide polymorphisms (SNPs), chromosomal rearrangements, the insertion of foreign genes, and alterations in methylation status of nucleic acids. These include infectious viruses, e.g. HIV and other retroviruses, jumping genes, e.g. transposons, and the identification of nucleic acids from recombinantly engineered organisms containing foreign genes, e.g. Roundup Ready plants.

The analysis of nucleic acids has a wide array of uses. For example, the presence of a foreign agent can be used as a medical diagnostic tool. The identification of the genetic makeup of cancerous tissues can also be used as a medical diagnostic tool, confirming that a tissue is cancerous, and determining the aggressive nature of the cancerous tissue. Chromosomal rearrangements, SNPs and abnormal variations in gene expression can be used as a medical diagnostic for particular disease states. Further, genetic information can be used to ascertain the effectiveness of particular pharmaceutical drugs, known as the field of pharmacogenomics.

Methods of extracting nucleic acids from cells are well known to those skilled in the art. A cell wall can be weakened by a variety of methods, permitting the nucleic acids to extrude from the cell and permitting its further purification and analysis. The specific method of nucleic acid extraction is dependent on the type of nucleic acid to be isolated, the type of cell, and the specific application used to analyze the nucleic acid. Many methods of isolating DNA are known to those skilled in the art, see for example the general reference Sambrook and Russell, 2001, "Molecular Cloning: A Laboratory Manual." For example, the prior art contains examples of chemically-impregnated and dehydrated solid-substrates for the extraction and isolation of DNA from bodily fluids that employ lytic salts and detergents and which contain additional reagents for long-term storage of DNA samples e.g. U.S. Pat. No. 5,807,527 detailing FTA paper and U.S. Pat. No. 6,168,922 detailing Isocard Paper. The prior art also contains examples of particle separation methods, e.g. U.S. RE 37,891.

While many nucleic acid purification procedures are well known and have been in existence for years, these procedures can be time consuming and may employ reagents that present dangers to those performing the purification. For example, it has long been known that DNA can readily be obtained in a purified form from a test sample using organic extraction procedures, but such procedures can require several extractions and therefore can be time consuming. Additionally, the use of some organic solvents is undesirable and dangerous if proper precautions are not followed.

Accordingly, there is a need for an efficient, effective and convenient method for isolating nucleic acids from cells and preparing cell-free nucleic acids (e.g., from body fluids) for analysis.

SUMMARY

The present disclosure relates to systems and methods for nucleic acid isolation. In particular, the present disclosure provides systems and methods for isolating low molecular weight circulating nucleic acids from bodily fluids (e.g., plasma).

Accordingly, in some embodiments, the present invention provides a method of isolating nucleic acids, comprising: a) contacting a sample comprising nucleic acids with a buffer comprising greater than 35% ethanol by volume; and b) isolating the nucleic acid. In some embodiments, the nucleic acid is in a cell and said buffer lyses said cell. In some embodiments, ethanol concentration in buffers is 30% or greater (e.g., 35%, 40%, 45%, 50%, 55%, 60%; +/−1%, 2%, 3%, 4%, 5% or fractions thereof or higher) by volume. For example, in some embodiments, the buffer comprises between approximately 35% and 40%, approximately 35% and 45%, approximately 35% and 50%, approximately 35% and 55%, approximately 35% and 60%, approximately 35% and 65%, approximately 40% and 45%, approximately 40% and 50%, approximately 40% and 55%, approximately 40% and 60%, approximately 40% and 65%, approximately 50% and 55%, approximately 50% and 60%, approximately 55% and 60%, and approximately 55% and 65%, + or −1%, 2%, 3%, 4%, or 5% of the aforementioned ranges. In some embodiments, the buffer comprises approximately 50% (e.g., +/−1%, 2%, 3%, 4%, 5%, 6%, 7%, 8%, 9%, or fractions thereof) ethanol. In some embodiments, ethanol concentration is approximately 60% or less. In some embodiments, isolating nucleic acid comprises the steps of i) binding nucleic acid to a solid support; ii) washing the solid support with a wash buffer; and iii) eluting the nucleic acids from the solid support. In some embodiments, the nucleic acid is a circulating DNA. In some embodiments, the circulating DNA is low molecular weight DNA (e.g., less than about 1000, 500, or 200 bases in length. In some embodiments, the sample is blood, blood products (e.g., plasma), serum, or urine. In some embodiments, the sample is from a subject and the presence, modification, or level of the nucleic acid in the sample is indicative of a disease state (e.g., cancer) in the subject. In some embodiments, the method further comprises the steps of analyzing the sample for the presence of the nucleic acid. In some embodiments, the analyzing comprises performing a nucleic acid detection assay selected from, for example, an amplification assay (e.g., real time PCR), a hybridization assay, a methylation detection assay (e.g., methylation specific PCR or heavy methyl PCR), or a sequencing assay.

In some embodiments, the present invention provides a method of isolating nucleic acids, comprising: a) contacting a sample comprising nucleic acids with buffer comprising approximately 40% to 60% ethanol by volume; and b) isolating the nucleic acid.

The present invention further provides a method of isolating nucleic acids, comprising: a) contacting a sample comprising nucleic acids with buffer comprising greater than 35% ethanol by volume; b) and isolating the nucleic acid by i) binding nucleic acid to a solid support; ii) washing the solid support with a wash buffer; and iii) eluting nucleic acids from the solid support.

The present invention additionally provides a method of isolating low molecular weight circulating DNA, comprising: a) contacting a sample comprising low molecular weight circulating DNA with buffer comprising greater than 35% ethanol by volume; and b) isolating the low molecular weight DNA from the sample.

The present invention also provides a method of isolating low molecular weight circulating DNA, comprising: a) contacting a sample comprising low molecular weight circulating DNA with buffer comprising greater than 35% ethanol by volume; b) isolating the low molecular weight DNA from the sample; and c) detecting the presence of the low molecular weight DNA in the sample using a amplification assay, where the presence, modification, or level of the nucleic acid in the sample is indicative of a disease in a subject from which the sample was obtained.

The present invention, in some embodiments, provides a kit, comprising: a) a buffer comprising approximately 35% or more ethanol by volume; b) a wash buffer; c) a solid support; and d) an elution buffer. In some embodiments, the solid support is a resin, a column, a particle, or a bead. Additional embodiments provide a kit, comprising: a) a buffer comprising approximately 45% to 65% ethanol by volume; and b) a solid support.

Further embodiments provide a kit, comprising: a) a buffer comprising approximately 50% ethanol by volume; and b) a solid support.

In some embodiments, the kits further comprise reagents for analysis (e.g., analysis by sequencing, amplification, hybridization, or methylation specific detection) of nucleic acids. Exemplary reagents include, but are not limited to, one or more sequencing primers, detection reagents, buffers, one or more nucleic acid probes, one or more amplification primers, nucleic acid polymerases, deoxynucleotides, bisulfite, methylation specific blocking probes, or one or more methylation specific amplification primers.

Certain embodiments of the present invention provide a composition, comprising: a circulating DNA; and a buffer comprising 35% or more ethanol by volume. In some embodiments, the nucleic acid is bound to a solid support.

Additional embodiments will be apparent to persons skilled in the relevant art based on the teachings contained herein.

DETAILED DESCRIPTION

The present disclosure relates to systems and methods for nucleic acid isolation. In particular, the present disclosure provides systems and methods for isolating low molecular weight circulating nucleic acids from bodily fluids (e.g., plasma).

DEFINITIONS

To facilitate an understanding of the present technology, a number of terms and phrases are defined below. Additional definitions are set forth throughout the detailed description. As used herein, "a" or "an" or "the" can mean one or more than one. For example, "a" widget can mean one widget or a plurality of widgets.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5 (carboxyhydroxyl-methyl) uracil, 5-fluorouracil, 5 bromouracil, 5-carboxymethylaminomethyl 2 thiouracil, 5 carboxymethyl-aminomethyluracil, dihydrouracil, inosine, N6 isopentenyladenine, 1 methyladenine, 1-methylpseudouracil, 1 methylguanine, 1 methylinosine, 2,2-dimethylguanine, 2 methyladenine, 2 methylguanine, 3-methyl-cytosine, 5 methylcytosine, N6 methyladenine, 7 methylguanine, 5 methylaminomethyluracil, 5-methoxyamino-methyl 2 thiouracil, beta D mannosylqueosine, 5' methoxycarbonylmethyluracil, 5 methoxyuracil, 2 methylthio N6 isopentenyladenine, uracil 5 oxyacetic acid methylester, uracil 5 oxyacetic acid, oxybutoxosine, pseudouracil, queosine, 2 thiocytosine, 5-methyl-2 thiouracil, 2-thiouracil, 4 thiouracil, 5-methyluracil, N-uracil 5 oxyacetic acid methylester, uracil 5 oxyacetic acid, pseudouracil, queosine, 2-thiocytosine, and 2,6 diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "circulating nucleic acid" as used herein, refers to a nucleic acid found in the circulatory system (e.g., blood or blood product such as plasma). Circulating nucleic acids can enter the blood stream by direct secretion from cells, by necrosis of cells or by apoptosis of cells. In some embodiments, circulating nucleic acids are cell free nucleic acids or "circulating free nucleic acids (cfDNA)".

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method. The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "amplicon" refers to a nucleic acid generated via amplification reaction. The amplicon is typically double stranded DNA; however, it may be RNA and/or DNA:RNA. The amplicon comprises DNA complementary to a sample nucleic acid. In some embodiments, primer pairs are configured to generate amplicons from a sample nucleic acid. As such, the base composition of any given amplicon may include the primer pair, the complement of the primer pair, and the region of a sample nucleic acid that was amplified to generate the amplicon. One skilled in the art understands that the incorporation of the designed primer pair sequences into an amplicon may replace the native sequences at the primer binding site, and complement thereof. In certain embodiments, after amplification of the target region using the primers the resultant amplicons having the primer sequences are used for subsequent analysis (e.g. base composition determination). In some embodiments, the amplicon further comprises a length that is compatible with subsequent analysis.

The term "amplifying" or "amplification" in the context of nucleic acids refers to the production of multiple copies of a polynucleotide, or a portion of the polynucleotide, typically starting from a small amount of the polynucleotide (e.g., as few as a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

As used herein, the term "solid support" refers to a substrate or other solid material that does not dissolve in aqueous solutions utilized in nucleic acid purification or isolation. For example, in some embodiments, solid supports are substrates utilized in nucleic acid purification and isolation. Examples include, but are not limited to, beads, particles, resins, chromatography columns, and the like. In some embodiments, solid supports are coated or functionalized with material that enhances nucleic acid binding.

As used herein, the terms "subject" and "patient" refer to any animal, such as a dog, a cat, a bird, livestock, and particularly a mammal, and preferably a human.

As used herein, the term "sample" is used in its broadest sense. In one sense, it is meant to include a representative portion or culture obtained from any source, including biological and environmental sources. Biological samples may be obtained from animals (including humans) and encompass fluids, solids, tissues, and gases. Biological samples include blood products, such as plasma, serum, and the like. Such examples are not however to be construed as limiting the sample types applicable to the present invention.

Embodiments of the Technology

Although the disclosure herein refers to certain illustrated embodiments, it is to be understood that these embodiments are presented by way of example and not by way of limitation.

In some disease states (e.g., colorectal cancer), levels of circulating DNA increase with the cancer stage. Thus, patients with Stage 1, which is the most curable stage, have the lowest amount of circulating DNA available for analysis. Therefore, it is important to isolate/recover as much as possible of this circulating DNA from plasma. Thus, methods for increasing yields of DNA for use in downstream assays (e.g., amplification or sequencing assay) of circulating DNA are needed.

During experiments conducted during the course of development of embodiments of the present disclosure, DNA was isolated from plasma using an automated sample handling device (Abbott m2000sp instrument) or manually using a DNA sample prep kit, which included 33.3% ethanol in the lysis or isolation buffer and wash buffer. Ethanol concentrations from 40% to 66% (40%, 45%, 50%, 55%, 60%, and 66%) were studied with mock samples, which were negative diluent spiked with 10 pg/ml of methylated septin9 DNA. Mock samples that were tested with 66% ethanol in the isolation buffer were cloudy, viscous and unable to capture microparticles. Samples that were tested with 60% and 55% of ethanol in the isolation buffer still looked cloudy but were able to capture microparticles, 50% of ethanol in the buffer provided an excellent result.

Embodiments of the present invention provide kits, systems and methods for isolating nucleic acids from biological samples (e.g., aqueous samples such as plasma, blood, urine, blood products and the like) using lysis/isolation and/or binding buffers with increased ethanol concentrations. In some embodiments, the plasma or other sample is free of cells or cellular material. The kits, systems, and methods described herein find use in research, screening, diagnostic, clinical, and therapeutic applications.

Accordingly, in some embodiments, the present invention provides kits, systems and methods for isolating cell-free low molecular weight DNA from biological samples (e.g., plasma). The present invention is not limited to a particular sample. Examples of biological samples (e.g., aqueous samples) suitable for use with the described methods include, but are not limited to, whole blood, blood products (e.g., plasma), urine, semen, lymph fluid, saliva, tears, mucus, etc.

The present invention is not limited to a particular source of nucleic acids for isolation. In some embodiments, nucleic acids are mammalian. In other embodiments, nucleic acids from foreign pathogens (e.g., viruses, bacteria, fungi, etc.) are isolated. In some particular embodiments, low molecular weight circulating nucleic acids are isolated and optionally detected. The present invention is not limited to particular molecular weights of DNA for isolation. In some embodiments, DNA that is isolated using the systems and methods described herein is less than approximately 20,000 bases (e.g., less than 15,000, less than 10,000, less than 5000, less than 4000, less than 3000, less than 2000, less than 1000, less than 500 bases, less than 400 bases, less than 300 bases, less than 250 bases, less than 200 bases, less than 150 bases, less than 100 bases, less than 50 bases, or less than 20 bases).

In some embodiments, the present invention provides compositions (e.g., reaction mixtures) systems and methods for improved recovery of low molecular weight circulating (e.g., cell free) nucleic acids. In some embodiments, the concentration of alcohol (e.g., ethanol) in buffers used for lysis or isolation of nucleic acids from samples (e.g., blood or plasma samples) and/or binding buffers is increased. In some embodiments, ethanol concentration in buffers is 30% or greater (e.g., 35%, 40%, 45%, 50%, 55%, 60%; +/−1%, 2%, 3%, 4%, 5% or fractions thereof or higher) by volume. For example, in some embodiments, the buffer comprises between approximately 35% and 40%, approximately 35% and 45%, approximately 35% and 50%, approximately 35% and 55%, approximately 35% and 60%, approximately 35% and 65%, approximately 40% and 45%, approximately 40% and 50%, approximately 40% and 55%, approximately 40% and 60%, approximately 40% and 65%, approximately 50% and 55%, approximately 50% and 60%, approximately 55% and 60%, and approximately 55% and 65%, + or −1%, 2%, 3%, 4%, or 5% of the aforementioned ranges. In some embodiments, the buffer comprises approximately 50% (e.g., +/−1%, 2%, 3%, 4%, 5%, 6%, 7%, 8%, 9%, or fractions thereof) ethanol. In some embodiments, ethanol concentration is approximately 60% or less.

In some embodiments, commercial nucleic acid purification kits and systems are utilized. Such systems function by binding nucleic acids to a solid support (e.g., column, bead, particle and the like). Contaminants are removed by washing with a wash buffer. Purified nucleic acids are then eluted from the support. In some embodiments, one or more steps of the nucleic acid isolation are automated (e.g., using automated sample handling or robotics).

Following isolation, nucleic acids may be analyzed using any suitable method. In some embodiments, the presence of pathogens is detected (e.g., blood or urine borne pathogens). In other embodiments, the presence of nucleic acid variants, polymorphisms, mutations, methylation status, etc. are detected (e.g., circulating nucleic acids associated with cancer).

In some embodiments, circulating nucleic acids associated with cancer are isolated and analyzed using the methods described herein. A variety of circulating or circulating free nucleic acids (cfDNA) have been shown to be associated with cancer (See e.g., Fleischhacker, Biochim Biophys Acta. 2007 January; 1775(1):181-232. Epub 2006 Oct. 7 and Chan et al., British Journal of Cancer (2007) 96, 681-685 Published online 20 Feb. 2007; Schwarzenbach et al., Nature 11:426 [2011]; each of which is herein incorporated by reference).

In some embodiments, circulating nucleic acids useful in prenatal diagnosis are isolated and detected using the methods described herein. Cell-free fetal nucleic acids circulating in the blood of pregnant women afford the opportunity for early, noninvasive prenatal genetic testing (See e.g., Sayres, Obstet Gynecol Surv. 2011 July; 66(7):431-42; herein incorporated by reference).

In some embodiments, microRNAs (e.g., microRNAs associated with disease) are detected.

In some embodiments, circulating nucleic acids are methylated and the detection methods include methylation-specific detection methods (e.g., those described below).

Examples of nucleic acid detection methods include, but are not limited to, sequencing, amplification, microarrays, probe binding and the like. Exemplary methods are described below.

A. Sequencing

In some embodiments, nucleic acid isolated using the system, compositions, and methods described herein (e.g., isolation/lysis buffers comprising at least 35% ethanol by volume (e.g., 40-60%, 45-55%, or approximately 50%) are further analyzed using sequencing methods.

Illustrative non-limiting examples of nucleic acid sequencing techniques include, but are not limited to, chain terminator (Sanger) sequencing and dye terminator sequencing.

A variety of nucleic acid sequencing methods are contemplated for use in the methods of the present disclosure including, for example, chain terminator (Sanger) sequencing, dye terminator sequencing, and high-throughput sequencing methods. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

B. Hybridization

In some embodiments, nucleic acid isolated using the system, compositions, and methods described herein (e.g., isolation/lysis buffers comprising at least 35% ethanol by volume (e.g., 40-60%, 45-55%, or approximately 50%) are further analyzed using hybridization methods.

Illustrative non-limiting examples of nucleic acid hybridization techniques include, but are not limited to, microarrays including, but not limited to: DNA microarrays (e.g., cDNA microarrays and oligonucleotide microarrays). A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

C. Amplification

In some embodiments, nucleic acid isolated using the system, compositions, and methods described herein (e.g., isolation/lysis buffers comprising at least 35% ethanol by volume (e.g., 40-60%, 45-55%, or approximately 50%) are further analyzed using amplification methods.

Nucleic acids may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), nucleic acid sequence based amplification (NASBA), methylation specific PCR (MSP), MethylLight PCR and HeavyMethyl PCR. Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat.

No. 0 684 315). Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

D. Detection Methods

Non-amplified or amplified nucleic acids (e.g., isolated using the system, compositions, and methods described herein (e.g., isolation/lysis buffers comprising at least 35% ethanol by volume (e.g., 40-60%, 45-55%, or approximately 50%)) can be detected by any conventional means. For example, the nucleic acids can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541, 205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DAB-CYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

In some embodiments, nucleic acids are detected and characterized by the identification of a unique base composition signature (BCS) using mass spectrometry (e.g., Abbott PLEX-ID system, Abbot Ibis Biosciences, Abbott Park, Ill.) described in U.S. Pat. Nos. 7,108,974, 8,017,743, and 8,017, 322; each of which is herein incorporated by reference in its entirety.

E. Methylation-Specific Detection

In some embodiments, nucleic acid isolated using the system, compositions, and methods described herein (e.g., isolation/lysis buffers comprising at least 35% ethanol by volume (e.g., 40-60%, 45-55%, or approximately 50%) are further analyzed using methylation-specific detection methods.

In some embodiments, methylation analysis utilizes bisulfite conversion or Methylation Sensitive Restriction Enzyme (MSRE). Bisulfite conversion methods utilize sequencing, primer-probes, primer-gel, or primer-array analysis.

One method for analyzing DNA for 5-methylcytosine is based on the specific reaction of bisulfite with cytosine which, upon subsequent alkaline hydrolysis, is converted to uracil which corresponds to thymidine in its base pairing behavior. 5-methylcytosine remains unmodified under these conditions. Consequently, the original DNA is converted in such a manner that methylcytosine, which originally cannot be distinguished from cytosine in its hybridization behavior, can now be detected, for example, by amplification and hybridization or sequencing. These techniques are based on base pairing which is now taken full advantage of.

An overview of methods of detecting 5-methylcytosines can be gathered from the following survey article: Rein, T., DePamphilis, M. L., Zorbas, H., Nucleic Acids Res. 1998, 26, 2255.

The bisulfite technology involves short specific fragments of a known gene, which are amplified subsequent to a bisulfite treatment and either completely sequenced (Olek, A. and Walter, J., Nat Genet. 1997, 17, 275-276) or individual cytosine positions are detected by a primer extension reaction (Gonzalgo, M. L., and Jones, P. A., Nucl. Acids Res. 1997, 25, 2529-2531, WO 9500669) or by an enzymatic digestion (Xiong, Z. and Laird, P. W., Nucl. Acids. Res. 1997, 25, 2532-2534). In addition, detection by hybridization has also been described (Olek et al., WO 99 28498).

Further publications dealing with the use of the bisulfite technique for methylation detection in individual genes are: Xiong, Z. and Laird, P. W. (1997), Nucl. Acids Res. 25, 2532; Gonzalgo, M. L. and Jones, P. A. (1997), Nucl. Acids Res. 25, 2529; Grigg, S. and Clark, S. (1994), Bioassays 16, 431; Zeschnik, M. et al. (1997), Human Molecular Genetics 6, 387; Teil, R. et al. (1994), Nucl. Acids Res. 22, 695; Martin, V. et al. (1995), Gene 157, 261; WO 97 46705; WO 95 15373 and WO 45560, herein incorporated by reference in their entireties. Using the bisulfate technique for detecting cytosine methylation in DNA samples is described in U.S. Pat. No. 7,524,629, herein incorporated by reference in its entirety.

Additional methods for determining methylation status are described, for example, in Lombaerts, M. et al. (2006) British Journal of Cancer. 94:661-671; Yoshiura, K. et al. (1995) Proc. Natl. Acad. Sci. 92:7416-7419; Lind, G. E. et al. (2004) Molecular Cancer 3:28; Kumagai, T. et al. (2007) Int. J. Cancer. 121:656-665; Hennig, G. et al. (1996) J. Biol. Chem. 271(1):595-602; Marchevsky, A. M. et al. (2004). Journal of Molecular Diagnostics 6:28-36; Reinhold, W. C. et al. (2007). Mol. Cancer. Ther. 6:391-403; Hu, X-C. et al. (2002) Life Sciences 71:1397-1404; or Nakata, S. et al. (2006) Cancer 106(10):2190-2199; each of which is herein incorporated by reference in its entirety. Commercial kits are also available for determination of promoter methylation status in tumor cells (e.g. Promoter Methylation PCR kit, from Panomics, Redwood City, Calif.).

Various methylation assay procedures are known in the art and can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-sensitive restriction enzymes.

The "HeavyMethyl™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, DMR, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase.

The term "MSP" (Methylation-specific PCR) refers to the art-recognized methylation assay described by Herman et al. (1996) Proc. Natl. Acad. Sci. USA 93: 9821-9826, and by U.S. Pat. No. 5,786,146.

MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, DMR, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, DMR, regions of genes, regions of markers, bisulfite treated DNA sequence, CpG island, etc.); TaqMan® or Lightcycler® probes; optimized PCR buffers and deoxynucleotides; and Taq polymerase.

F. Data Analysis

In some embodiments, a computer-based analysis program is used to translate the raw data generated by the detection assay (e.g., the presence, absence, or amount of a given nucleic acid) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence or absence of a nucleic acid) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

E. Systems and Kits

In some embodiments, the present invention provides kits and systems for the isolation, and analysis of nucleic acids (e.g., low molecular weight circulating DNA). In some embodiments, kits include reagents necessary, sufficient or useful for detection of nucleic acids (e.g., reagents, wash buffers, elution buffers, controls, instructions, etc.). In some embodiments, kits comprise solid supports for binding nucleic acids (e.g., beads, resins, columns, particles, etc.). In some embodiments, kits comprise isolation/lysis buffers comprising at least 35% ethanol by volume (e.g., 40-60%, 45-55%, or approximately 50%).

For example, in some embodiments, the present invention provides a kit, comprising: a) a buffer comprising 35% or more ethanol by volume; b) a wash buffer; c) a solid support; and d) an elution buffer. In some embodiments, the ethanol is present in the buffer at a concentration of approximately 40% to 60%. In some embodiments, the ethanol is present in the buffer at a concentration of approximately 45% to 55%. In some embodiments, the ethanol is present in buffer at a concentration of approximately 50%. In some embodiments, the solid support is selected from, for example, a resin, a column, a particle, or a bead.

In some embodiments, the kit further comprises reagents for analysis of nucleic acids. For example, in some embodiments, the analysis is selected from, for example, sequencing, amplification, hybridization, or methylation specific detection. In some embodiments, the reagents are selected from, for example, one or more sequencing primers, detection reagents, buffers, one or more nucleic acid probes, one or more amplification primers, nucleic acid polymerases, deoxynucleotides, bisulfite, methylation specific blocking probes, and or one or more methylation specific amplification primers.

In some embodiments, kits comprise reagents for the isolation of nucleic acids and their analysis by sequencing. For example, in some embodiments, kits comprise reagents for isolation of nucleic acids (e.g., isolation/lysis buffers comprising at least 35% ethanol by volume (e.g., 40-60%, 45-55%, or approximately 50%), solid supports, wash buffers, elution buffers, etc.), and reagents for performing a sequence assay (e.g., one or more sequencing primers, detection reagents, buffers, instruments (e.g., spectrometers), controls, etc.).

In some embodiments, kits comprise reagents for the isolation of nucleic acids and their analysis by hybridization. For example, in some embodiments, kits comprise reagents for isolation of nucleic acids (e.g., isolation/lysis buffers comprising at least 35% ethanol by volume (e.g., 40-60%, 45-55%, or approximately 50%), solid supports, wash buffers, elution buffers, etc.), and reagents for performing a hybridization assay assay (e.g., one or more nucleic acid probes, detection reagents, buffers, instruments (e.g., spectrometers), controls, etc.).

In some embodiments, kits comprise reagents for the isolation of nucleic acids and their analysis by amplification. For example, in some embodiments, kits comprise reagents for isolation of nucleic acids (e.g., isolation/lysis buffers comprising at least 35% ethanol by volume (e.g., 40-60%, 45-55%, or approximately 50%), solid supports, wash buffers, elution buffers, etc.), and reagents for performing a amplification assay (e.g., one or more amplification primers, nucleic acid polymerases, deoxynucleotides, buffers, detection reagents, instruments (e.g., spectrometers), controls, etc.).

In some embodiments, kits comprise reagents for the isolation of nucleic acids and their analysis by methylation specific detection methods. For example, in some embodiments, kits comprise reagents for isolation of nucleic acids (e.g., isolation/lysis buffers comprising at least 35% ethanol by volume (e.g., 40-60%, 45-55%, or approximately 50%), solid supports, wash buffers, elution buffers, etc.), and reagents for performing a methylation specific detection assay (e.g., bisulfite, methylation specific blocking probes, one or more methylation specific amplification primers, nucleic acid polymerases, deoxynucleotides, buffers, detection reagents, instruments (e.g., spectrometers), controls, etc.).

In some embodiments, kits comprise one or more containers that comprise reagents, solid supports, buffers (e.g., wash buffers, lysis/isolation buffers, elution buffers, etc.), controls, and the like. In some embodiments, each component of the kit is packaged in a separate container. In some embodiments, the containers are packed and/or shipped in the same kit or box for use together. In some embodiments, one or more components of the kit are shipped and/or packaged separately.

In some embodiments, systems include automated sample and reagent handling devices (e.g., robotics).

EXPERIMENTAL

The following examples are provided in order to demonstrate and further illustrate certain preferred embodiments and aspects of the present invention and are not to be construed as limiting the scope thereof.

Example 1

Materials and Methods

1. Manual Sample Extraction

Manual sample preparation was performed to extract and concentrate the target DNA molecules to make the target accessible for amplification, and to remove potential inhibitors using the Abbott mSample Preparation System$_{DNA}$ kit. The DNA extraction kit employs magnetic particles to capture nucleic acids, which are then washed to remove unbound sample components. The nucleic acids were eluted and the non-methylated cytosine residues were then converted via treatment with bisulfite salts in a thermal cycler. The nucleic acids were re-isolated and purified using the Abbott mSample Preparation System$_{DNA}$ kit. The eluted samples were transferred to a 96-well optical reaction plate, along with a prepared PCR reaction mix. The plate was then transferred to Abbott m2000rt instrument.

Both DNA extraction and post-bisulfite purification steps utilize ethanol addition to the Lysis buffer of the Abbott mSample Preparation System$_{DNA}$ kit for DNA binding. The first step is DNA extraction, which involves DNA binding with magnetic particle and lysis buffer, followed by washing and elution. The second step is bisulfite treatment that involves treatment of the eluted DNA with bisulfite salts at the following conditions: 99° C. 5 min, 50° C. for 25 min, 99° C. 5 min, 50° C. 1 hour 25 min, 99° C. 5 min, 50° C. 4 hours 55 min, hold 4° C. The third step is post-bisulfite purification that involves DNA binding with magnetic particle and lysis buffer, follow by wash and elution prior to PCR.

2. Real-Time PCR

A primer mix consisting of 1 forward primer and 1 reverse primer targeting Septin9 was used to amplify methylated Septin9 targets, which were detected with a Septin9-specific probe. Annealing of primer to the unmethylated allele of the Septin 9 gene locus is prevented by a methylation-specific blocker oligonucleotide, which specifically binds to the unmethylated allele. The PCR reaction is designed to amplify only the methylated Septin 9 targets and the amplified targets were detected with a methylation specific probe. Beta-actin amplicons were generated with a primer set targeting the Beta-actin sequence and were detected with a Beta-actin specific probe. This serves as the Internal Control for the assay. The amplified region of beta-actin is not subject to methylation, so the cytosines in this region are always modified by bisulfite.

In addition to primers and probes, the PCR reaction consists of 13 Units AmpliTaq Gold enzyme, 7 mM magnesium chloride (as activation reagent) and oligonucleotide reagent (containing 0.6 mM dNTPs, 0.05 uM ROX reference dye, Tris, KCl and antimicrobials).

The real-time amplification/detection reaction was carried out on an Abbott m2000rt instrument with the following cycling conditions: 1 cycle at 93° C. 30 min; 50 cycles at 93° C. 30 s, 62° C. 5 s and 58° C. 35 s. Fluorescence measurements were recorded during the read step (58° C.) of the 50 cycles.

Example 2

Ethanol Titration in the DNA Lysis/Binding Buffer

A range of ethanol concentrations (45%, 50%, or 55%) in the lysis buffer were utilized, compared to 33% ethanol in the lysis buffer (the typically used ethanol concentration) in both Step 1 (DNA extraction) and Step 3 (Post-bisulfite purification). The samples contained diluted sonicated methylated Septin9 DNA in negative plasma at low target levels (10 pg/ml, 25 pg/ml, and 100 pg/ml). Each of these low level targets was tested in replicates of 10 for a total of 30 samples in each study. Overall sample positivity is defined as the percentage of positive samples detected over total number of samples tested.

This example demonstrates that increasing ethanol concentration in the lysis buffer in the DNA sample prep kit increases DNA yields from plasma.

TABLE 1

Septin 9% Sample Detection

| % Ethanol in lysis buffer | N | Overall sample positivity (%) |
|---|---|---|
| 33% | 30 | 67% |
| 45% | 30 | 87% |
| 50% | 30 | 80% |
| 55% | 30 | 77% |

Example 3

Sensitivity with Colorectal Cancer Specimens

The ethanol concentration in the lysis buffer at 50% was further tested with CRC positive samples, comparing to ethanol concentration of 33% for sensitivity with patients samples. Sixteen colorectal cancer specimens were tested with increased ethanol in the lysis buffer and compared to the same specimens tested with Abbott RealTime mS9 Colorectal Cancer assay. The Abbott RealTime mS9 Colorectal Cancer assay uses the Abbott m2000sp instrument for automated processing of plasma samples and it normally has 33% ethanol in the lysis buffer.

This example demonstrates that increasing ethanol concentration from 33% to 50% in the lysis buffer is able to increase sensitivity for 3 stages of colorectal cancer.

TABLE 2

Performance of sensitivity with colorectal cancer specimen

| 33% Ethanol in lysis buffer | 50% Ethanol in lysis buffer |
|---|---|
| Stage 1 = 4/8 = 50% | Stage 1 = 6/8 = 75% |
| Stage II = 3/5 = 60% | Stage II = 5/5 = 100% |
| Stage III = 1/3 = 33% | Stage III = 3/3 = 100% |

Example 4

Specificity with Patient Specimens

The impact on specificity was evaluated with increased ethanol in the lysis buffer with negative samples collected from people over 50 years old that have had normal colonoscopy results. A total of 50 samples was tested with 1 sample invalid due to an Abbott m2000rt instrument error. In this population, the specificity of the assay was 93.9%.

TABLE 3

Specificity performance

| N | Number not detected | Specificity % |
|---|---|---|
| 49 | 46 | 93.9 |

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:
1. A method of isolating nucleic acids, comprising:
   a) contacting a biological sample comprising cells with a lysis buffer comprising greater than 35% ethanol by volume;
   b) contacting said sample of step a) with a solid support that binds cell-free nucleic acid wherein said solid support is a magnetic particle wherein said magnetic particle is coated or functionalized with material that enhances nucleic acid binding;
   c) washing said solid support of step b) with a wash buffer; and
   d) eluting nucleic acid from said solid support to generate isolated nucleic acid.
2. The method of claim 1, wherein said ethanol is present in said lysis buffer at a concentration of approximately 40% to 60%.
3. The method of claim 1, wherein said ethanol is present in said lysis buffer at a concentration of approximately 45% to 55%.
4. The method of claim 1, wherein said ethanol is present in said lysis buffer at a concentration of approximately 50%.
5. The method of claim 1, wherein said nucleic acid is a circulating DNA.
6. The method of claim 5, wherein said DNA is less than 1000 bases in length.
7. The method of claim 5, wherein said DNA is less than 500 bases in length.
8. The method of claim 5, wherein said DNA is less than 200 bases in length.
9. The method of claim 1, wherein said sample is selected from the group consisting of blood, blood products, serum, and urine.
10. The method of claim 1, wherein said sample is from a subject and the presence of said nucleic acid in said sample is indicative of a disease state in said subject.
11. The method of claim 10, wherein said disease state is cancer.
12. The method of claim 1, further comprising the step of analyzing said sample for the presence of said nucleic acid.
13. The method of claim 12, wherein said analyzing comprises performing a nucleic acid detection assay selected from the group consisting of an amplification assay, a hybridization assay, a methylation status detection assay, and a sequencing assay.
14. The method of claim 13, wherein said amplification is real time PCR and said methylation status detection assay is methylation specific PCR or heavy methyl PCR.
15. A composition, comprising: a circulating DNA; a magnetic particle wherein said magnetic particle is coated or functionalized with material that enhances nucleic acid binding; and a lysis buffer comprising 35% or more ethanol by volume in a mixture with a biological sample comprising one or more cells.

16. The composition of claim 15, wherein said ethanol is present in said lysis buffer at a concentration of approximately 45% to 55%.

* * * * *